United States Patent
Hadeishi

[11] 3,957,375
[45] May 18, 1976

[54] VARIABLE THICKNESS DOUBLE-REFRACTING PLATE

[75] Inventor: Tetsuo Hadeishi, Berkeley, Calif.

[73] Assignee: The United States of America as represented by the United States Energy Research and Development Administration, Washington, D.C.

[22] Filed: July 23, 1974

[21] Appl. No.: 491,095

Related U.S. Application Data

[63] Continuation-in-part of Ser. No. 336,579, Feb. 28, 1973, Pat. No. 3,811,778, and a continuation-in-part of Ser. No. 442,280, Feb. 13, 1974, Pat. No. 3,914,054.

[52] U.S. Cl..................................... 356/85; 350/149; 356/97
[51] Int. Cl.² .......................................... G02F 1/29
[58] Field of Search .................. 356/85, 86, 87, 97; 350/149, 151, 160 R, 161

[56] References Cited
UNITED STATES PATENTS
2,753,754   7/1956   Le Clair........................... 350/149 X
3,495,912   2/1970   Hooper et al. ................ 350/149 UX

OTHER PUBLICATIONS
Hadeishi et al., "Hyperfine Zeeman Effect Atomic Absorption Spectrometer for Mercury," Science, Vol. 174, oct. 22, 1971, pp. 404–407.

*Primary Examiner*—John K. Corbin
*Assistant Examiner*—F. L. Evans
*Attorney, Agent, or Firm*—Dean E. Carlson; Leonard Belkin; Cornell D. Cornish

[57] ABSTRACT

This invention provides an A.C., cyclic, current-controlled, phase retardation plate that uses a magnetic clamp to produce stress birefringence. It was developed for an Isotope-Zeeman Atomic Absorption Spectrometer that uses polarization modulation to effect automatic background correction in atomic absorption trace-element measurements. To this end, the phase retardation plate of the invention is a variable thickness, photoelastic, double-refracting plate that is alternately stressed and released by the magnetic clamp selectively to modulate specific components selected from the group consisting of circularly and plane polarized Zeeman components that are produced in a dc magnetic field so that they correspond respectively to Zeeman reference and transmission-probe absorption components. The polarization modulation changes the phase of these polarized Zeeman components, designated as σ reference and π absorption components, so that every half cycle the components change from a transmission mode to a mode in which the π component is blocked and the σ components are transmitted. Thus, the Zeeman absorption component, which corresponds in amplitude to the amount of the trace element to be measured in a sample, is alternately transmitted and blocked by a linear polarizer, while the circularly polarized reference components are continuously transmitted thereby. The result is a sinusoidally varying output light amplitude whose average corresponds to the amount of the trace element present in the sample.

8 Claims, 2 Drawing Figures

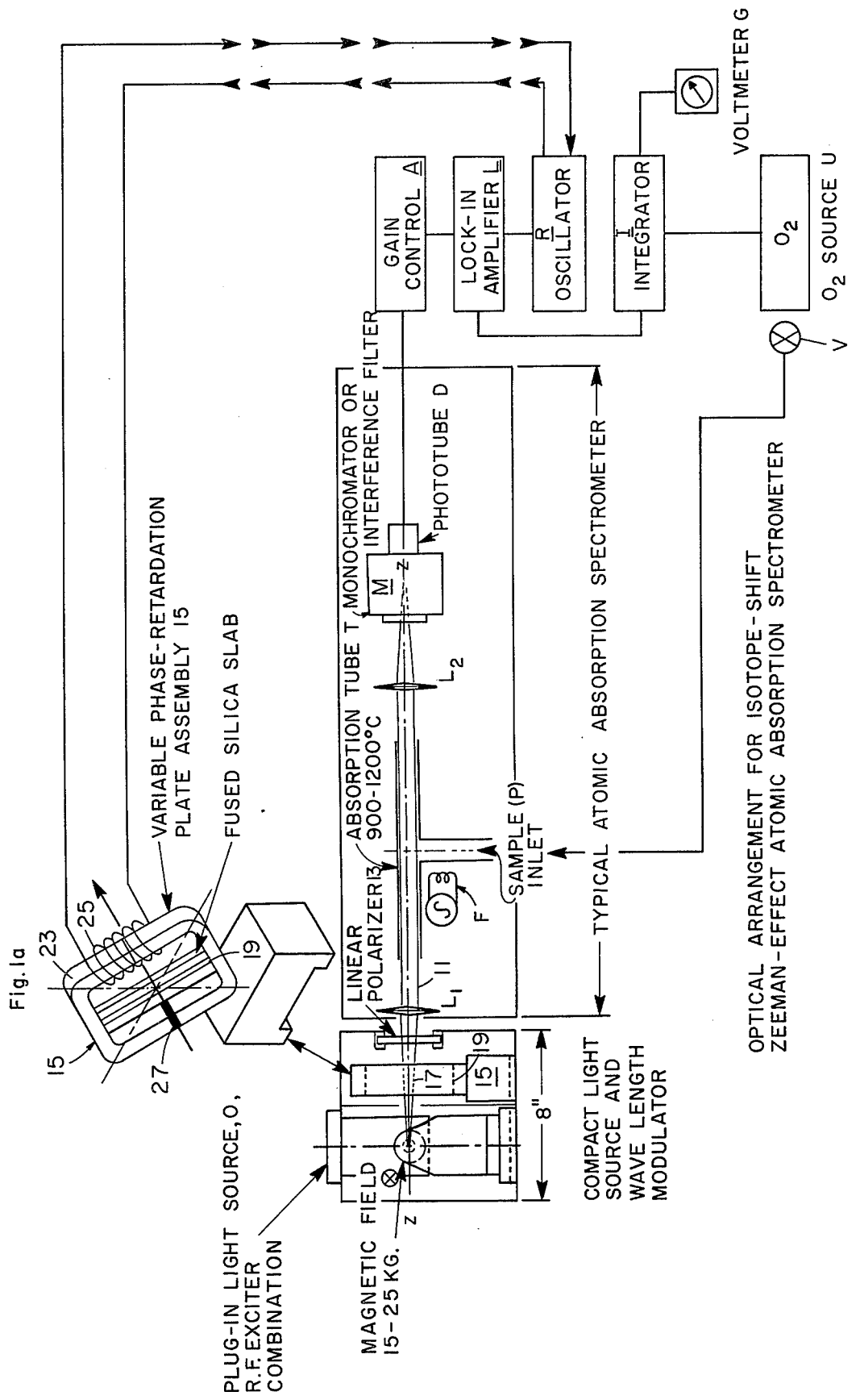

VARIABLE THICKNESS DOUBLE-REFRACTING PLATE

CROSS REFERENCE TO RELATED APPLICATIONS:

This application is a continuation-in-part of U.S. application Ser. No. 336,579, filed Feb. 28, 1973, now U.S. Pat. No. 3,811,778; U.S. application Ser. No. 442,280, filed Feb. 13, 1974, now U.S. Pat. No. 3,914,054.

BACKGROUND OF THE INVENTION:

This invention was made in the course of, or under a contract with the United States Atomic Energy Commission.

In applications involving polarized light, modulating devices that alternately transmit light of differing polarization are useful in conjunction with phase-sensitive detection to enhance signal-to-noise ratio. Such devices include modulators of the Kerr or Pockels cell variety, the rotating polarizers of the first above-cited application, and fused silica stressed piezoelectric crystals. However, each of these devices has limitations. For example, Kerr cells have low transmission, and the materials used in Pockels cells strongly absorb ultraviolet. Rotating modulators work well at low frequencies, but frequencies more suitable for phase sensitive detection are not easily attained. On the other hand, the piezoelectrically-stressed fused silica modulators known heretofore have required operation at a resonant frequency of the silica plate because of limitations imposed by the driving crystals, and these fixed frequencies (50 kHz typical) have often been inconvenient for many phase-sensitive detection applications. It is also advantageous to provide polarization modulation with a non-rotating phase retardation plate for an Isotope-Zeeman Atomic Absorption Spectrometer. More particularly, it is advantageous to provide high-frequency polarization modulation in place of the low frequency rotating plate of U.S. Pat. No. 3,811,778, which employs as a light source a single separated isotope of mercury in a dc magnetic field.

SUMMARY OF THE INVENTION:

This invention provides a current-controlled phase retardation plate that uses a magnetic clamp to produce stress birefringence. More particularly, this invention provides an A.C., cyclic, current-controlled, phase retardation plate device having, in one embodiment, a specific magnetic clamp whose axis is at an angle of 45° to the D.C. magnetic field of the light source in a Isotope-Zeeman Atomic Absorption Spectrometer. The device is driven at an audio frequency by a pair of drive coils on a transformer core to produce substantially (or close to) zero stress on the retardation plate only when the magnet isn't energized. To this end, the retardation plate is substantially uniformly stressed in a cycle from zero to half-wave retardation a few hundred times a second by an oscillator having an audio-amplifier and a D.C. bias source that supply the necessary drive current at up to 100 watts for producing a specific modulation. In one application, light comes from a single separated isotope of Hg in a uniform, constant, D.C. magnetic field, and the light is directed normal to the D.C. magnetic field to produce a $\pi$ Zeeman component that is polarized (linearly) parallel to the direction (vertical) of the D.C. magnetic field and $\sigma$ ($\sigma^+$ and $\sigma^-$) Zeeman components that are polarized (linearly) perpendicular to the D.C. magnetic field. To modulate the $\pi$ and $\sigma$ components in accordance with this invention, the current-controlled phase retardation plate takes the place of the rotating polarization modulation means of the first abovecited patent application. In connection with the phase retardation plate of this invention, therefore, one embodiment comprises a phase retardation plate means for receiving and selectively transmitting the described specific polarized Zeeman components along an axis in successive stages. An A.C., cyclic, current-controlled, magnetic clamp means applies varying pressures to the phase retardation plate means for effecting the alternate, periodic, phase retardation of a plane polarized $\pi$ Zeeman component, and the alternate transmission thereof through and blocking by a linear polarizer in accordance with the pressures applied to the phase retardation plate means. With the proper selection of uniaxial strain and frequencies, as described in more detail hereinafter, the desired high frequency polarization modulation is achieved in an Isotope-Zeeman Atomic Absorption Spectrometer.

It is an object of this invention, therefore, to provide an improved light polarization modulation means having a current controlled magnetic clamp.

The above and further novel features and objects will appear more fully from the following detailed description of one embodiment when the same is read in connection with the attached drawings, and the novel features will be pointed out in the appended claims.

BRIEF DESCRIPTION OF THE DRAWING:

FIG. 1 is a partial three-dimensional view of one embodiment of this invention;

FIG. 1a is a partial three-dimensional view of the magnetic clamp of FIG. 1.

DESCRIPTION OF THE PREFERRED EMBODIMENT:

It is known that cubic crystals and amorphous solids become birefringent if subject to mechanical stress. This effect is described by M. Born etal in "Principles of Optics" Pergamon, N.Y., 1970, and in J. Amer. Ceramic Soc., 21, 27(1938). Since strain is proportional to stress in linear materials, the formula therefor, as written in Am. Instit. of Physics Handbook, McGraw Hill, 1972, pp. 6–232, and 233, is:

$$\Gamma = \frac{CTl}{\lambda}, \text{ where } \Gamma \frac{\delta}{2\pi}$$

is the retardation in wave lengths, T is the applied tensile stress in the Newtons/meter$^2$, l is the length of the light path in the retardation means, $\lambda$ is the wave length, and C is the stressoptical constant in Brewsters ($10^{-12}m^2/N$). It follows, therefore, in accordance with the new use of this invention that uniaxial stress or strain of cubic crystals and amorphous solids, such as a fuzed silica cube, produce birefringence, which involves a piezo or photoelastic effect capable of producing in a D.C. mode a fixed phase retardation plate. This invention hereinafter described utilizes a phase retardation plate of this type, to which in accordance with this invention a current-controlled electromagnet externally and mechanically applies opposite forces that selectively squeeze the ends of the phase-retardation plate along the plate axis when the magnet is energized, and release the phase retardation plate from being squeezed when the electromagnet is not energized. Thus, the phase retardation plate has zero stress externally applied thereto by the electromagnet when the magnet isn't energized, and a substantial predetermined stress externally applied thereto when the magnet is energized.

In accordance with one embodiment of this invention, (FIG. 1–1a), Zeeman $\sigma$ and $\pi$ light components from a single separated isotope are directed normal to the dc magnetic field of U.S. Pat. No. 3,811,788, the light components are focused in a light beam 11, and then the focused beam is transmitted toward a linear polarizer means 13 after having passed through a plate selected from the group consisting of a fused silica, and a lithium fluoride quartz retardation plate means 15 having a vertical stress axis along the beam optical path 17. Such plates are normally singly refracting, rectangular-shaped plates having parallel ends 19 that are equally spaced from and on opposite sides of a Z—Z axis, and normal to the opposite plate faces. A pair of C-magnets 23 having coils 25 presses across a gap 27 against the opposite ends 19 of the plate means 15 and are caused to press wth more or less force against the plate means according to variations in current in the pair of coils 25 around the magnets. The plate means 15 is squeezed thereby across the magnet gap 27 and thus alternately subjected to strain and correspondingly exactly to change the phase and direction of polarization of the focused light in beam 11 by ½ retardation, e.g. from ¼ $\lambda$ to ¾ $\lambda$.

In a long thin plate of isotropic transparent material, such as fused silica, sinusoidally varying strains of the order of $10^{-5}$ are required to produce a desired modulated birefrigence, but this strain is considerably below the breakage point thereof. The same applies to a plate made of lithium fluoride for vibrational modes, typically up to $10^{-4}$, to produce useful angular apertures of up to 50° total cone angle, which makes the device superior to Pockels or Kerr cells. A description of the theory behind the time periodic modulation of the plate 15 is given in "Journal of the Optical Society of America", Vol. 59, Number 8, August 1969, Part I, p 950–954, by James C. Kemp. In this connection it will be understood, however, that the required uniaxial strain for providing the desired piezooptic or photoelastic birefringence modulation in a time periodic manner, is provided in accordance with this invention by a novel arrangement, comprising the described sinusoidally varying current in coils around the described two C magnets that are spaced across a gap 27 to squeeze and release the plate 15 in one directio at audio or acoustic frequencies in the range of up to 200 k Hz. Also, the axis of the plate 15 is arranged at 45° to the direction of the dc magnetic field in which the Zeeman components are produced.

As will be understood in more detail hereinafter, a standard linear polarizer is used in tandem with the modulator, as described in the above first cited application. Alternately, polarizing film for ultraviolet light, such as are applied to glass or plastic, may be used. Even when coated with a protective layer of lacquer, they exhibit a higher transmittance and better extinction than calcite crystal polarizers or stretched - polyvinyl alcohol films. They are described in detail in "Journal of the Optical Soc. of Am." Vol. 51, Number A, September 1961, pp 1008–1010. Also, a standard monochromator M or interference filter and a standard photo-tube detector D for light from a source $\sigma$ is used for detecting Hg in a fish sample P heated in a furnace F. An automatic gain control A, an oscillator R, a lock-in amplifier L, an integrator I, a valve V, a gas source U, an absorption tube T, and a voltmeter complete a typical unit.

In operation, when the light is directed from the source in the direction parallel to the magnetic field, there are only two $\sigma$ components ($\sigma^+$ and $\sigma^-$) and no $\pi$ component. On the other hand, when the light is directed normal to the magnetic field in accordance with this invention, there are $\pi$ and $\sigma^+\sigma^-$ components. In this latter case the $\pi$ component is polarized (linearly) parallel to the magnetic field and the $\sigma$ components are both linearly polarized perpendicular to the magnetic field. In this case one can pass either the monitoring $\pi$ or the reference $\sigma$ components by placing the stress axis of the retardation plate at 45° with respect to the magnetic field direction and the linear polarizer, which follows the retardation plate either parallel or perpendicular to the magnetic field direction. To switch between the monitoring and reference line, one applies compressional force to the quartz plate to give retardation of ½ wave length.

Advantageously, the Isotope-Zeeman Atomic Absorption Spectrometer of this invention has an electrodeless single separated Hg light source located at a point on the central axis of the linear polarizer 13, which is on a line through the center of the opposite parallel faces of the retardation plate means 15, and separated a distance from the plate means 15.

The beam is transported through lenses L, one of which is shown schematically for focusing and collimating the light in the form of parallel beam 11 containing the $\pi$ and the right and left linearly polarized $\sigma^-$ and $\sigma^+$ components so that all the light entering the plate means 15 from source 0 will leave in the form a parallel beam 11 containing reference and absorption components whose directions of polarization and phases have been selected by the retardation plate means 15. When the light is directed along the direction normal to the magnetic field, the $\pi$ component is linearly polarized parallel to the field and the $\sigma^+$ and $\sigma^-$ components are both linearly polarized perpendicular to the field.

After passing through the retardation plate 15 and the linear polarizer, which transmits the $\pi$ and $\sigma$ components and alternately periodically blocks the $\pi$ component, the light passes through a monochromator M or an interference filter for amplitude detection by a phototube that alternately detects the components for comparing their amplitudes as a measure of the mercury in the vaporized fish sample P. At least one linear polarizer and one cycle of increasing or decreasing pressure applied to phase retardation means 15 is required in order to obtain sufficient change in the phase or direction of polarization of the two components to select and filter out one of the components while transmitting the other component to the detector, and the increasing pressure applied must be reduced to zero to obtain the effect of comparing the two components in the detector.

To obtain the desired filtering, separation and comparison, the beam 11 is transported through the phase retardation means 15 while increasing and decreasing pressures are applied thereto repeatedly in closely spaced cycles at a frequency and pressure up to but not exceeding the elastic limit of the phase retardation means 15. Advantageously, the beam is transported sequentially from the source 0 along the Z—Z axis through a vaporized fish sample P that is heated in a furnace F having $O_2$ circulated therethrough to reduce smoke therein, and thereafter the beam is passed through means 15 and 13 to detector D.

A practical arrangement for accomplishing the desired filtering for separating and comparing the desired Zeeman effect components in beam 11 is illustrated in the drawing, where the heretofore known retardation of a beam 11 having one Zeeman component on top of the absorption profile of the contaminant to be detected is accomplished by applying pressure to a quartz plate 15 that is sandwiched between two laminated C-magnets 23. These magnets are activated by passing a sinusoidally varying current from a conventional wall socket or portable generator through the coils 25 wound about the magnet cores so that the current when increasing causes the magnet attractions to increase across gap 27. The decreasing portion of the current cycle causes decreasing magnetic attraction. The increasing and decreasing magnetic attraction, causes the magnets to increase and decrease the pressure on the quartz plate retardation means 15 in a direction transverse to the Z—Z axis of path 17 between the opposite ends 19 of the plate, these ends being parallel to the plane of the Z—Z axis of path 17. This varying pressure increases and decreases to alternately change the phase retardation or direction of polarization in the reference light component and the absorption light component, so that the linear polarizer 13 allows the $\pi$ component to pass with the other components or alternately periodically to be blocked.

The detector D, which is a photomultiplier, produces an output signal having a D.C. component that is proportional to the total light intensity incident on the phototube. The automatic gain control A senses this D.C. component and automatically adjusts its gain so that if the total light intensity either increases or decreases, a given amount of mercury in the absorption tube results in the same A.C. output signal, which is supplied to a lock-in amplifier L that uses as a reference the same 200 Hz oscillator R that actuates the retardation means. The voltage output from the amplifier L is integrated by integrator I, which is connected to an $O_2$ gas valve V to feed $O_2$ from $O_2$ source U to the absorption tube T containing the test sample heated in furnace F. A digital voltmeter G reads out the voltage from the integrator as a measure of the mercury in the test sample. As is conventional, suitable zero control settings provide calibration in the absence of a sample in the absorption tube.

The pressure on plate 15 is varied while the sample P is vaporized in the optical path 17 of beam 11 along the Z—Z axis for the measurement of the quantity of the undesirable trace element present in the sample P, and the matrix may be animal, vegetable, mineral, water or air. To this end, there is employed for the sample P the furnace F that is shown in FIG. 1 the operating parameters being chosen such that the signal that results doesn't depend upon the contaminant sample matrix. To better control the combustion process in furnace F, a high current low voltage heating system is used for heating the sample P in furnace F, and the furnace temperature is controlled using a silicon controlled rectifier (SCR), and $O_2$ stream circulating through the furnace, and a logic, such as known in the art, to cause a transformer to supply the required high current without core saturation. Also, a suitable lamp source 0 is used, while a suitable detector D is used for the detection of the described Zeeman components for the measurement of the contaminant in the sample. It will be understood, therefore, that this invention is broadly useful in the field of environmental health, safety and research for detecting trace metal elements, such as mercury, arsenic, lead and cadmium in the basic life sustaining substances of air, water and soil, as well as the products derived therefrom.

The following are examples of one embodiment of this invention:

EXAMPLE I

The phase retardation plate is about 0.5 cm by 1 cm by 7.5 cm and is made of fused silica that is held in the grip of a magnetic clamp made from a split-C-transformer core so as to hold the plate at 45° to the direction of a dc magnetic field in which Zeeman $\sigma$ and $\pi$ components are produced for modulation and transmission through a linear polarizer. The length of the plate is chosen so that there is a 0.5 mm gap between the magnet poles on the side nearest the silica. The clamp is held by foam rubber and silicon rubber cement in a tub-like holder at an angle of 45° to the vertical, since this angle is necessary for the device to function in the polarization modulation mode desired. The soft suspension mechanically isolates the clamp from the holder. When the device is being driven at an audio frequency, this isolation is necessary. This means of support also maintains contact between the pole faces opposite the silica plate without a rigid connection; thus the silica plate is subject to stress only when the magnet is energized. A lucite guide keeps the poles parallel on the side nearest the plate. The device is actuated by a pair of drive coils wound on a transformer core so that when the plate is not stressed, it is passive. In this mode the linear polarizer transmits both the $\sigma$ and $\pi$ components at 45° to the direction of the dc magnetic field. When the plate is stressed, the plane of polarization of the $\pi$ and $\sigma$ components are rotated 90°. In this latter mode only the $\sigma$ components are transmitted by the linear polarizer since the $\pi$ component is perpendicular to the dc magnetic field and the $\sigma$ components are parallel to the dc magnetic field.

EXAMPLE II

The arrangements of Example I are repeated and various means are employed for holding the fused silica plate in place. In one case, the ends of the plate are held by an epoxy to the transformer core while the plate is positioned with a jig. Suitable resins, comprise Shell Chemical Corporation epoxy trademarked EPON 828 and epoxy resin known as Bakelite ERL 2774, Dow Resin X-2633.4, Borden's Epiphen Epoxides, Ciba Asaldite, Devoe and Reynolds Epi-Rez 510 or polyglycidal novolak resins or such diapoxides as RDGE (resorcinol Diglycidyl ether) described in U.S. Pat. No. 2,892,849. Various boron trifluoride-amine complexes may be used as first curing agents, i.e., curing catalysts, such as EPON curing Agent BF3-400, as well as monoethylamine, triethanolamine, urea, ammonia, piperdine, hexamethylene-tetramine, and phenolic complexes. Other second catalysts for such resins, comprise dicyandiamide, cyanamid, melamine, cyanuric chloride, triethanolamine borate, 4,4'-diamino diphenyl sulfone, methylene dianiline, m-phenylene diamine, phthalic ahydride, pyromellitic dianhydride and maleic anhydride. The amount of first catalyst used will vary in the range of 1–10 parts of catalyst per hundred parts of epoxy resin. The amount of second catalyst used will vary from 5–50 parts per hundred parts of epoxy resin.

EXAMPLE III

The arrangements of Example II are repeated, and a thin pad of lucite is placed between each end of the plate and the core. Before using the current control for the retardation plate, it is viewed between crossed polarizers while applying a D.C. drive current to check the uniformity of the stress application. In this example, the cycle of retardation is from zero-to half-wave retardation a few hundred times per second. To this end, an oscillator, audio amplifier, and a D.C. bias supply provides the necessary drive currents.

Light linearly plane polarized at 45° with respect to the stress axis falls upon the input end of the retardation plate. The polarization of the light emerging from the plate is given as a function of applied stress from vertically polarized at zero wave (no stress) to horizontal at half-wave, or from horizontally polarized at zero wave (no stress) to vertical at half-wave. With no stress, the polarization is unaltered. Increasing stress generates first elliptically, then circularly and finally linearly polarized light emerging from the plate, this light being polarized perpendicularly to the incident light when one has half-wave retardation.

By placing the retardation plate between properly aligned crossed polarizers, there is zero transmission at zero current. As the current is increased, the transmission increases until the retardation is half-wave, and then falls off with further increase in current, the results being measured using Glan-Thompson prisms as polarizers relative to the transmitted intensity obtained with parallel polarizers. The drop off in transmission intensity at high current is due to saturation of the transformer core, and thus the stress.

EXAMPLE IV

The arrangement and steps of Example III are repeated with an A.C. current superimposed on a properly chosen bias current so that the transmitted intensity cycles between zero and maximum as the retardation plate modulates the polarization of the incident light. The transmitted light intensity at 2537A from a separated mercury isotope discharge lamp in a constant magnetic field is detected with a photomultiplier monitor. With increasing frequency of operation in the phase retardation plate from 100 Hz to 250 Hz, the percent modulation of the transmitted light declines. At 1 kilohertz and 100 watts power, the modulation was 35%, and as the frequency was reduced, the power requirement for maximum modulation also declined.

EXAMPLE V

The steps and apparatus of Example IV are repeated in both the static and dynamic phase retardation plate modes. Unlike piezo-electric devices, the magnetically clamped, current controlled phase retardation plate of this invention can be used in a static mode as a variable phase retardation plate. In addition, this plate is used over a broad range of wavelengths by simply adjusting the drive currents. Moreover, this phase retardation plate is used to switch between linearly polarized components or circularly polarized components with an electrical adjustment of the current control.

EXAMPLE VI

The steps and apparatus of Example V are repeated using the Isotope-Zeeman Atomic Absorption Spectrometer of the above-cited patent for detecting Hg in a vaporized sample of fish, wherein the current controlled, magnetically clamped, phase retardation plate of this invention is substituted for the rotating plate of the cited patent, and operated by alternately periodically squeezing and releasing the plate to transmit and block the selected Zeeman components as desired. To this end, a single, separated, mercury isotope, electrodeless light source in a constant, uniform, dc, vertical magnetic field was used with suitable lenses to produce a beam of light containing Zeeman reference $\sigma$ components at right angles to the dc magnetic field, and a plane polarized $\pi$ Zeeman absorption component parallel to the magnetic field. Then, all the components were focused along a Z—Z axis in an optical path through a sample of vaporized fish containing mercury. As understood from the above-cited patent, the polarized $\pi$ and polarized $\sigma^+$ and $\sigma^-$ Zeeman components are close enough in frequency respectively to be equally scattered, and the $\sigma^+$ and $\sigma^-$ components are separated from the $\pi$ component enough in frequency respectively to be differentially absorbed by the mercury in vaporized fish. Detection of the mercury in the sample is based on the fact that the reference Zeeman light component can be alternately blocked and transmitted selectively, the light and mathematics of such systems being known from the cited patent.

EXAMPLE VII

Focused light is taken through conventional lenses from a conventional 100 ma plug-in electrodeless light source having a high voltage R.F. exciter combination (up to 300V) in a uniform, constant, continuously variable magnetic field of 15–25 KG in a direction normal to the light taken from the source. The light source is a single separated $^{204}$Hg light source. The light container is ultra-violet transmitting quartz, such as contemplated in the above-cited patent. A polarized probe component on top of the peak absorption profile thereof by mercury was transmitted along the Z—Z axis in a uniform beam through the quartz pressure plate and linear polarizer means, and focused on the light detector, which is a photomultiplier tube photo detector.

The photomultiplier, which has a filter for selecting the 2537 A spectral line of the mercury lamp, operates at 600 volts.

If it is impossible to bring the reference and probe beams into balance due to the presence of a new lamp, the drive electrodes are modified, and an aperture is mounted in front thereof to select light from the center of the finger that extends into the magnet gap, rather than at the edge thereof. The optical alignment is done with the furnace cold but with the lamp operating.

In this example, the frequency of the A.C. signal applied to the coils of the magnets is 200 Hz, so that the A.C. signal from the photo detector at this frequency is conveniently extracted with a conventional lock-in amplifier, such as described in Lawrence Berkley Laboratory Report (U. of Calif.) LBL-2084. To this end an audio amplifier having a D.C. supply of 5 amps is employed. The amplitude of this signal measures the quantity of the trace element Hg in the absorption tube of the furnace containing the vaporized sample, with the furnace acting at 800° – 900° as a mini-incinerator. An oscilloscope is used to trace the 200 Hz signal from the oscillator through the magnetic clamp of the quartz plate means. An audio amplifier, such as well known in the art, is used for the oscillator.

The phase — retardation plate means is tuned by conventional mean with a 200 Hz oscillator amplitude duo-dial at 00.45 and a D.C. clamp dial at 87. To establish the proper settings with the lamp source lit, a polarization compensator plate is turned in the optical path along the Z—Z axis, until the monitoring and reference components seen by the photo detector are equalized in the absence of a sample. The D.C. supply is reset to optimize lock-in output and rezero this output with the polarization compensator plate. Then the plate is properly adjusted.

This example is used to measure the mercury content of seafood and other food stuffs; Table I gives a comparison of the results of the measurements compared with more conventional techniques.

In general, at the 1 ppm level, one can expect that the measurements will be straight forward. One can easily use relatively small samples of 10 to 15 mg and still get large signals without problems of smoke. Typically, the system noise below 10 mg permits detection of 0.2 ng with a signal to noise ratio of unity and a flow rate of 40 cc/min with smokey samples.

Before starting a series of measurements, the apparatus is cleared. To this end, the system is out gassed with a 2 liter/min $O_2$ flowing through a hot furnace for one or two minutes. Then the system is calibrated with a known standard sample, e.g. a five microliter sample of 1 ppm solution containing 5 ng of mercury. With an average reading for these samples of 1.000 volt, then the calibration constant is 5 ng/1 volt. If some other sample gives 0.5 Volts, then the mercury content is 5 ng/volt × (0.5 volts) = 2.5 ng.

EXAMPLE VIII

The steps of Example VII are repeated, with the vaporized sample on the optic axis of the transmitted light beam after a fused silica quartz pressure plate means and the linear polarizer means.

EXAMPLE IX

The steps of Example VII are repeated, with the vaporized sample on the optic axis of the transmitted light beam before a lithium fluoride quartz pressure plate means and the linear polarizer means. The lithium fluoride and fused silica plates are equivalent.

EXAMPLE X

The steps of Example VII are repeated with a phase-retardation plate module containing a magnet squeezer clamp means that applies a sinusoidally varying stress to a plate of fused quartz, which is approximately 3 in. long, 0.5 in. wide and 0.25 in. thick. The focused light beam from the $^{204}$Hg light source penetrates the quartz at the center of the slab, while a mask blocks all the light that did not pass through the quartz. The clamp is driven with an A.C. current superimposed upon a D.C. bias current. By adjusting the magnitude of the A.C. current with a conventional transformer means, the stress is just adequate to make the quartz function as a half-wave plate at the extreme maximum amplitude end of the A.C. cycle while at the other or minimum extreme end, the stress is substantially zero.

The stress does not actually pass through zero, since this would cause the squeezer clamp means to lose contact with the ends of the quartz slab, and this would produce audible chatter and unstable operation. As described in Lawrence Berkley Lab Report LBL-2084, and shown in FIG. 7 thereof, the electronics for driving the clamp, comprise a 200 Hz oscillator, connected seriation to a Bogen brand audio amplifier and the magnetic clamp drive coil, which also is connected to a D.C. supply.

EXAMPLE XI

The steps of Example X were repeated with lamps containing a buffer gas at a pressure of a few Torr confined in a magnetic field of 15 KG in the following quartz envelope shapes for the selected, single, separated $^{204}$Hg isotope: spherical paddle-shaped with reservoir, cylindrical symmetric, and dumbbell-shaped. The latter was the most successful shape for "raw" gaseous, liquid or solid samples, wherein the described apparatus was successful in suppressing the effects of spurious absorption by interfering substances. To this end, the effect of background absorption was removed by measuring the difference between the absorption of probe light, which had a wavelength falling on the absorption of the reference light, and reference light, which had a wavelength falling outside the Hg absorption line of interest.

EXAMPLE XII

The steps of Example XI are repeated with the flameless furnace of the second above-cited application.

EXAMPLE XIII

The steps of Example XII are repeated with the respective use of the three linear polarizers described in the cited September 1961 Journal of the Optical Society of America article. To this end one linear polarizer is a commercially available Polacoat Company Polacoat brand film applied to glass or fused quartz to produce polarized light at wavelengths of at least as short as 215 m$\mu$. The film is described in U.S. Pat. No. 2,400,877. Other suitable films are described in U.S. Pat. Nos. 2,481,830 and 2,544,659. To this end, the supporting quartz is rubbed along parallel lines to produce minute scratches parallel to the rubbing direction. A solution of one or more 920 dyes is applied to the rubbed material, then dried in a controlled fashion. Presumably the conjugated double-bond structures of the azo dye molecule line up preferentially along the rubbing direction, resulting in greater absorption for light polarized in that direction. As a final step, the surface is treated with an acidic solution, often a metallic salt, such as stannous chloride, which has the effect of increasing dichroism and producing a more neutral color. One film, is 1/16 in. thick on 5-in. diam. discs of commercial-grade fused quartz supplied by Engelhard Industries, Inc. under designations DL 40 and 10UVR, the latter having a density such that the transmittance of the film is 32% in unpolarized light at 546 $\mu$m, or 44%.

EXAMPLE XIV

The steps of Example XII are repeated using a clear 0.0014-in. thick stretched polyvinl alcohol (PVA) linear polarizer, such that a 0174 $\lambda$ retardation at any wavelength in the region of interest is obtained.

EXAMPLE XV

The steps of Example XII are repeated using a 0.005 in. thick linear polarizer made from synthetic - phlogopite mica, which is essentially transparent over the entire ultraviolet and visible spectrum. The transmittance is 80% or more (including reflection losses from 200 to 400 m$\mu$).

EXAMPLE XVI

The steps of Example XI are repeated in which the photomultiplier detector is connected seriation to an automatic gain control, a lock-in amplifier connected to the 200 Hz oscillator as a reference, an integrator connected to the $O_2$ valve for circulating $O_2$ through the furnace, and a digital voltmeter whose reading indicates the amount of the mercury in the sample tested.

The automatic gain control functions to correct for fluctuations in the light output of the lamp, and for attenuation of the light beam by smoke. To this end, it is necessary that the amplitude of the A.C. signal that reaches the lock-in amplifier due to the presence of mercury in the absorption tube, which contains the sample that is heated in the furnace, depends only on the amount of mercury present, not upon the light output of the lamp, nor the degree to which smoke is attenuating the light. It is noted that a given quantity of mercury in the sample absorbs a given absolute amount of light. That fraction is independent of the intensity of the incident light, but the absolute amount of light energy absorbed is proportional to the incident light intensity. Since the photomultiplier responds to the absolute light level, if no steps are taken to compensate for this phenomenon, a given quantity of mercury, along with enough smoke to absorb half the light would give the same indication as half that amount of mercury with no smoke; this situation would be entirely unacceptable.

The automatic gain control accomplishes the necessary compensation. To do this, it senses the D.C. component of the signal coming from the photomultiplier. This component is proportional to the total light intensity incident on the phototube. The automatic gain control automatically adjusts its gain so that if the total light intensity either increases or decreases, a given amount of mercury in the absorption tube results in the same size A.C. signal at the output of the automatic gain control circuit, which supplies the input signal to the lock-in amplifier.

The lock-in amplifier amplifies the audio frequency signal contained in the output of the photomultiplier detector due to the presence of mercury in the absorption tube. In effect, the amplifier measures the signal level corresponding to mercury plus background absorption, the signal level, which corresponds to background absorption alone, and then generates a voltage proportional to the difference between the two. Since the "background", and the "mercury plus background" signal are presented to the lock-in amplifier alternately at the same terminal, the amplifier is also provided with information as to when one signal is coming in, and when the other is. This information is provided by the 200 Hz reference signal from the 200 Hz oscillator. This signal, after amplification, is the signal used to drive the magnetic clamp. Consequently, it contains information as to when the clamp is applying stress and when it is not. This is equivalent to information as to when the background, and when the mercury plus background signals are being supplied to the lock-in amplifier.

A mixer takes the difference between the background, and the mercury plus background signals to provide a D.C. output voltage that is proportional to this difference; it is followed by a D.C. amplifier. Its gain is controlled by an appropriately labelled switch. When the difference between the two signals is small, the voltage output from the mixer and hence the amplifier may fluctuate quite a bit due to random instabilities in the system. What is significant is not the instantaneous, but rather the average voltage output of the amplifier. Thus, conventional averaging means are provided to electronically average (damp) the output having a switch for a selection of averaging times from 10 milli seconds to 10 seconds. This time-averaged output is then presented to a D.C. output voltmeter. It is the voltage indicated on this meter that serves to indicate the measure of the quantity of mercury in the absorption tube at any given time.

The voltage to the meter may be zeroed, or a constant voltage added or subtracted by use of "zero offset" controls while there is no sample in the absorption tube. The sensitivity of the meter is selectively chosen to be either 1 volt or 10 volts full scale for measuring the vaporized sample when it is in the absorption tube.

The integrator is connected to the lock-in amplifier. One might think that if the output of the lock-in amplifier were displayed on a chart recorder, the height of the peak that the recorder would display when a sample is run could be used as a measure of the samples mercury content. Indeed, under certain circumstances, it can. If one is comparing the mercury content of two identical types of samples, the peak height gives good relative measure of the amount of mercury present in each. In the more usual case, though, a given sample, which is frequently a solid, is being compared with a known volume of standard solution. As a function of time, the solid and the solution release the mercury quite differently. Consequently, even if both contain the same amount of mercury, the peak heights are likely to differ. One can make quite general arguments, however, that the peak areas would be the same. The integrator electronically measures the peak area.

The integrator is controlled by a spring-loaded three-position switch. When the switch is depressed, integration begins. If one were to plot the voltage applied to the input of the integrator, one would find that the output at any time is proportional to the area under the curve for the period of time that the integrate switch is depressed. When the integrate switch is released, it springs back to the "hold" position. To clear the integrator, the switch must be raised to the "reset" position.

The output of the integrator is read by a digital voltmeter that reads from −1.999 to +1.999 volts. It quite commonly happens that an overflow occurs, in which case the integrator rises above 2 volts. When this happens, it may be desirable to turn the integrator calibrate control down to reduce the integrator output instead of reducing the lock-in gain.

The three-position integrate switch also controls the solenoid valve on the oxygen supply. When the switch is in the "reset" or the "integrate" position, the $O_2$ is flowing; in the "hold" position, it is turned off.

EXAMPLE XVII

The steps of Example XIII are repeated, and in order to employ the described $\sigma^+$ $\sigma^-$ and $\pi$ Zeeman components, the light from the source is taken at right angles to the magnetic field.

In this case, the three lines are obtained so that the center line is plane polarized parallel to the magnetic field and at right angles to the other outside lines, as is well known in the art. The center line lies on the absorption curve for mercury, as described in application Ser. No. 288,801 filed Sept. 13, 1972, by the inventor herein. In this case, the quartz pressure plate means 15 is alternately changed from zero, where it is singly refracting, to ½ λ retardation, and the remainder of the apparatus is as described above.

The above has described examples of an IZAA isotope-Zeeman, atomic absorption system for use with simple samples. The heart of the technique lies in the method by which the probe and reference components are generated, and the mode by which these components are distinguished from each other. Thus, this invention can be used for the wide variety of samples described in Table II.

The described invention has the advantage that mechanically rotating parts are eliminated, so that problems of run-out and end-play are eliminated. Also, the expense of accurately machining and operating a rotating quarter-wave plate are eliminated. Furthermore, the shift between the lines, being electrically actuated, can be at a much higher rate per second, and this has the advantage of enhancing accuracy and/or of reducing the time during which the comparison of the Zeeman components need be made.

This invention further has the advantage of automatically correcting for interferences in atomic absorption spectroscopy by selecting, monitoring, and comparing the relative intensities of Zeeman components with a filter system utilizing a quartz plate and a linear polarizer. By applying varying pressure to the quartz plate, the desired selection, monitoring and comparing are accomplished easily, accurately, efficiently and economically in a trouble-free manner. While the device is being specifically developed and used in the laboratory in an environmental program to detect mercury in the atmosphere, water, and food, final development should provide a low-cost and highly sensitive instrument for environmental monitoring of various substances.

Table 1

Comparison of Isotope-Shifted Zeeman-Effect Technique to Other Conventional Methods

| Sample source and identification | Lab where tested | Method used | Their results (ppm) | Our results in 10 sec (ppm) |
|---|---|---|---|---|
| National Bureau of Standards Reference 1571 (Orchard leaves) | NBS | Spark source mass spectrometer, neutron activation, chemical analysis with atomic absorption | 0.2 | 0.20 ± 0.04 |
| National Marine Fisheries Service, Seattle, Washington | | | | |
| Sample 614-1200 (fish protein concentrate) | NMES | Wet Chemistry | 0.72 | 0.72 ± 0.05 |
| Sample 628-0400 (fish protein concentrate) | NMES | Wet Chemistry | 0.59 | 0.53 ± 0.01 |
| Sample S-433 (wet cod) | Phoenix Mem. Gulf Atomic NMFS | Neutron activation Neutron activation FDA method (wet chem) 0.48, 0.45 | 0.49 0.48 0.58 | 0.45 ± 0.02 |
| Sample S-430 (wet halibut) | Phoenix Mem. Gulf Atomic NMFS | Neutron activation Neutron activation FDA method (wet chem.) 0.10, 0.14 | 0.12 0.13 0.09 | 0.14 ± 0.02 |
| National Canners Association Aceton powder tuna (white meat) | NCA | Wet Chemistry | 2.48 | 2.08 ± 0.02 |
| Univ. of California At Davis | LBL | X-ray fluorescence | 12.0 ± 2.0 | 10.0 ± 0.3 |
| UCD Control mare liver | LBL | Neutron activation | 11.0, 14.0 | |

TABLE II

PRELIMINARY PROTOCOL FOR THE EVALUATION OF THE ISOTOPE-SHIFT ZEEMAN-EFFECT ATOMIC ABSORPTION SPECTROMETER (IZAA)

Anticipated use of the IZAA will include the following sample types:

Air, air filters, fresh water, sea water, sewage effluent, silt and bottom sediments, soil, fresh and dehydrated plant and animal tissue.

The evaluation program will be conducted as follows:
1. Types of samples
   a. Aqueous solutions of organic and inorganic mercury compounds.
   b. Solutions of organic and inorganic mercury compounds in organic solvents.
   c. Soil spiked uniformly with inorganic and/or organic mercury compounds.
   d. Dried alfalfa spiked with known amounts of organic and inorganic mercury compounds.
   e. Air samples containing known amounts of metallic mercury (prepared for air samples saturated with mercury vapor under standard conditions).
   f. Sea water samples spiked with organic and inorganic mercury compounds.
   g. Selected samples from a – f, with possible interfering elements or compounds added.
2. All samples will be prepared at appropriate concentration intervals from 0.001 – 1.00 ppm.
3. Sample preparation and handling.
   Sample preparation will be carried out in our Quality Assurance Laboratory. The samples will be stored and handled according to established procedures.
4. The number of individual samples to be analyzed for each sample kind will be determined in accordance with statistical principles. Statistical methods will be used to evaluate the analytical data.

5. Information regarding instrument stability, down time, and other pertinent instrument parameters will be carefully collected during the entire period of evaluation.

6. Similar evaluation programs will be conducted for cadmium and lead as soon as the attachments required for the modification of IZAA become available.

What is claimed is:

1. Polarization modulation apparatus for use with an Isotope-Zeeman Atomic Absorption Spectrometer system employing a constant magnetic field and a single separated mercury isotope source for producing Zeeman spectral light components, comprising reference light and absorption light having different frequencies that are transmitted through a gas containing a biologically dangerous contaminant, a modulation means and a linear polarizer means so that the reference and absorption light produce a sinusoidally varying signal whose amplitude varies in accordance with the amount of said contaminant in said gas, comprising:

a. first phase-retardation plate means for receiving and selectively transmitting said light components along an axis to the linear polarization means in successive stages; and b. means for applying selectively variable frequency pressures to said first means in said system for effecting the selective transmission of said reference and absorption light through said system along said axis in accordance with the pressures applied to said first means for facilitating the comparison of said reference and absorption light to determine the amount of said contaminant in said gas.

2. The apparatus of claim 1 in which said first phase-retardation plate means comprises:

photoelastic plate means for receiving said reference and absorption light and selectively changing the direction of polarization and the phase retardation thereof for transmitting the same along said axis in a particular direction of polarization.

3. The apparatus of claim 2 in which said means for applying varying pressures to said first means varies the thickness of said plate means alternately to provide first and second directions of polarization and corresponding phase retardations to the reference and absorption light transmitted along said axis to said second means.

4. The invention of claim 3 in which said means for applying said pressures, comprises:

a. first C magnet means;

b. second C magnet means arranged next to said first C magnet means across a gap with said variable thickness double refracting plate sandwiched between said first and second C magnetic means; and c. variable current winding means around said magnet means for altering at audiofrequencies the magnetic attraction between said first and second C magnet means for altering the pressure on the plate means for selectively changing the direction of said polarization and the corresponding phase retardation of said reference and absorption light transmitted from said first to said linear polarizer means.

5. The apparatus of claim 3 in which said plate means is a crystal selected from the group consisting of fused silica and lithium fluoride for alternately changing the phase retardation from ¼ λ to ¾ λ.

6. In the method for selecting Zeeman light components having different frequencies forming a beam that is successively received and transmitted through a biologically dangerous contaminant by a system comprising transparent plate means and linear polarizer second means, the step of imposing and substantially removing to zero variable pressure on the plate means selectively to transmit said components through said linear polarizer means.

7. The method of claim 6 in which three spectral lines are taken from a source at right angles to a magnetic field, the center line being plane polarized parallel to the magnetic field and at right angles to the outside lines and the center line lying on the peak of the absorption curve for mercury, and the plate means is alternately changed from zero where it is singly refracting, to ½ λ retardation for selectively alternately transmitting said Zeeman components.

8. The method of claim 7 in which the amplitude difference in said respective Zeeman components transmitted corresponds to the amount of said contaminant in said gas, said variable pressure selectively alternately causing one Zeeman light component to be transmitted and one Zeeman light component to be blocked.

* * * * *